United States Patent [19]
Guerra

[11] 4,187,082
[45] Feb. 5, 1980

[54] DENTAL FINISHING STRIPS

[76] Inventor: Humberto R. Guerra, 4800 Marque Dr., New Orleans, La. 70120

[21] Appl. No.: 479,729

[22] Filed: Jun. 17, 1974

[51] Int. Cl.² ............................ A61C 3/06; A61C 3/12
[52] U.S. Cl. ........................................ 51/295; 51/298; 51/407; 433/229
[58] Field of Search ................ 51/407, 295, 293, 298, 51/299; 32/45, 58

[56] References Cited

U.S. PATENT DOCUMENTS

| | | | |
|---|---|---|---|
| 217,300 | 7/1879 | Starr | 51/407 |
| 449,930 | 4/1891 | Dubey | 51/298 |
| 522,211 | 7/1894 | How | 32/46 |
| 1,414,447 | 5/1922 | Tone | 51/295 |
| 1,657,784 | 1/1928 | Bergstrom | 51/295 |
| 1,988,065 | 1/1935 | Wooddell | 51/295 |
| 2,015,658 | 10/1935 | Bezzenberger | 51/293 |
| 2,712,987 | 7/1955 | Storrs | 51/298 |
| 2,881,065 | 4/1959 | Reuter | 51/298 |
| 2,899,288 | 8/1959 | Barclay | 51/298 |
| 3,136,614 | 6/1964 | Kuzmick | 51/298 |
| 3,246,969 | 4/1966 | Embree et al. | 51/295 |

FOREIGN PATENT DOCUMENTS 69491  8/1928  Sweden .

*Primary Examiner*—Donald J. Arnold
*Attorney, Agent, or Firm*—James B. Lake, Jr.

[57] ABSTRACT

A flexible plastic strip having oppositely disposed faces, one of said faces being smooth and the other defining a smooth middle portion and opposite end portions diagonally coated with an abrasive. The width of the finishing strip is made approximately the same as an average distance from gum line contact point of two adjacent teeth, that is about 7 millimeters. The diagonal coatings make it possible to reduce and smooth to tooth level repairs of any size without ridging the repairs.

3 Claims, 2 Drawing Figures

U.S. Patent

Feb. 5, 1980

4,187,082

DENTAL FINISHING STRIPS

This is a copending application of my similarly titled patent application, Ser. No. 303,468, filed Nov. 3, 1972 now abandoned.

The invention relates generally to finising strips for removing surplus material and smoothing dental repairs and establishing the margins thereof.

Heretofore dental finishing strips have had their ends fully coated on a side by respectively different grades of abrasive material. The width of a strip was made to correspond with the smallest possible repair area between adjacent teeth, that is about 4 millimeters. If the repair were larger it had to be finished in two steps which resulted in ridging the repairs.

It is an object of the invention to provide a finishing strip for finishing a repair in one step and without ridging.

Figure 1:
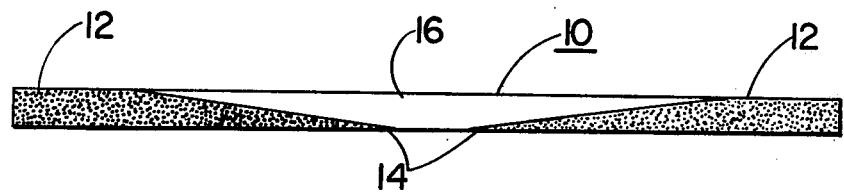
Figure 2:
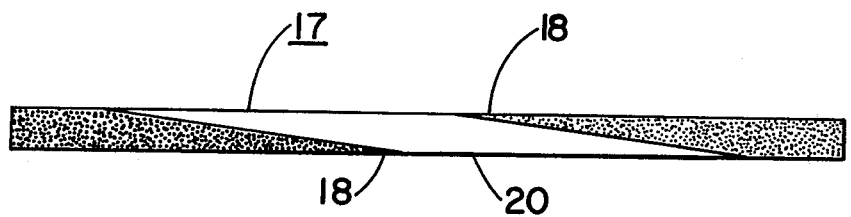

Other objects and a fuller understanding of the invention may be had be referring to the following discription, claims and drawings in which:

FIG. 1 is a side elevational of the coated side of one specie of the invention, and FIG. 2 is similar to FIG. 1 of a second specie of the invention.

Referring to FIG. 1, a first specie of the invention comprises a flexible strip 10 coated on one side and on oppositely disposed areas 12 in a longitudinally spaced diagonal arrangement. The points or origins 14 of the diagonal coating are directly opposed across the longitudinal spacing and define a center portion 16 of the finishing strip. The coatings comprise abrasives.

Referring to FIG. 2, a second specie of the invention is similar to the first except that the points or origins 18 of the oppositely disposed coated areas 12 are diagonally opposed across an uncoated center area 20.

In both species the coatings are respectively of different grades of abrasive material, one for removing surplus material and the other for smoothing the surface of the repairs.

In use, a first specie finishing strip is inserted by its uncoated center portion between the repaired and adjacent teeth, and by oppositely disposed ends adjusted longitudinally for a diagonal width of the roughest grade of coating to cover the repairs. The strip is alternately pulled back and forth within the diagonal width range of the strip to abrade the repair approximately down to coincide with the surrounding tooth surface in one step. The finishing strip is then pulled to position the smoothest grade of abrasive coating on the oppositely disposed diagonal to cover said repairs, for smoothing them in one step as described in removing surplus repair material.

The use of the second specie finishing strip is similar to that of the first specie except that the strip has to be withdrawn from between the teeth and the ends reversed after removing surplus repair material in order to smooth the repairs.

The advantage of the first specie of the invention is that it does not have to be withdrawn and reinserted with reversed ends to smooth the repairs.

The advantage of the second specie is that the diagonal coating of abrasive coatings are easier to apply.

For a suitable plastic strip, a well-known Dupont mylar material is recommended. The top surface of the 'mylar' is softened by an application of polyester resin. Grit that may be cuttle, aluminum oxide or zirconium silicate is applied to the softened surface which is allowed to harden under variable conditions of temperature and curing.

More specifically, grit is applied to "MYLAR" strips as follows: a binder known commercially as 46960 comprising 30 parts copolyester in 70 parts methyl ethyl ketone is mixed with aluminum oxide and the mixture ball milled to a suitable grit size in the liquid resin. The constituents can range from 40–60 parts respectively to 60–40 parts. Add to this mixture 2.5 parts of RC 805, a curing agent, for each 30 parts of solid copolyester in the mixture and apply a whole as a coating to the "mylar" strips. Let dry and cure for about an hour at 75 degrees C. Then dilute another 2.5 parts of RC 805 to a water thin consistency with methyl ethyl ketone and apply as a size to the coated strips. After drying the size, cure the sized and coated strips overnight at about 75 degrees C. The abrasive coated strips are now ready for use. All the parts are by weight, and all constituents are obtainable from the E. I. Dupont de Nemours & Co. of Wilmington, Delaware 19898.

What is claimed is:

1. A dental finishing strip for smoothing and finishing dental work to the level of external tooth structure comprising:
   a. an elongated flexible plastic strip, having oppositely disposed ends, a thickness to fit between adjacent teeth, a width to extend between a gum line and a contact point between adjacent teeth, and a length between said oppositely disposed ends for manual holding and pulling back and forth by said ends between adjacent teeth; and
   b. abrasive grit coating means in two different grades fixed on a side of said flexible plastic strip and respectively extending in a different grade longitudinally and diagonally from each of said oppositely disposed ends toward the center thereof to define tapering and longitudinally opposed grit coated areas, tapering and transversely opposed grit coated and uncoated areas, and an uncoated center area therebetween, for inserting said flexible plastic strip between adjacent teeth and manually pulling said strip in a back and forth motion between said center and an end in sequence, the grit covered areas in sequence removing surplus and smoothing the rest of said dental work without ridging.

2. A dental finishing strip as described in claim 1 wherein said coatings of abrasive materials taper to the same edge of said finishing strips.

3. A dental finishing strip as described in claim 1 wherein said coatings of abrasive materials taper to opposite edges of said finishing strip.

* * * * *